United States Patent [19]

Kohayakawa et al.

[11] 4,196,979
[45] Apr. 8, 1980

[54] METHOD AND DEVICE FOR DETECTING DISTANCE BETWEEN EYE-EXAMINING INSTRUMENT AND EYE

[75] Inventors: Yoshimi Kohayakawa; Isao Matsumura, both of Yokohama, Japan

[73] Assignee: Canon Kabushiki Kaisha, Tokyo, Japan

[21] Appl. No.: 832,827

[22] Filed: Sep. 13, 1977

[30] Foreign Application Priority Data

Oct. 16, 1976 [JP] Japan .............................. 51-124289
May 30, 1977 [JP] Japan .............................. 52-63065

[51] Int. Cl.² .............................................. A61B 3/14
[52] U.S. Cl. ......................................... 351/7; 351/13; 354/62; 356/3
[58] Field of Search ................ 354/62; 351/1, 6, 7, 351/13, 14, 16; 356/3, 8, 20

[56] References Cited

U.S. PATENT DOCUMENTS

| | | | |
|---|---|---|---|
| 3,871,772 | 3/1975 | Munnerlyn | 351/6 X |
| 3,904,280 | 9/1975 | Tate, Jr. | 351/1 |

*Primary Examiner*—F. L. Evans
*Attorney, Agent, or Firm*—Toren, McGeady and Stanger

[57] ABSTRACT

A method and a device for making the distance between a human eye and an eye-examining instrument coincide with a preset distance. A miniature light source disposed on the image end of an objective lens of the instrument illuminates the eye. The light specularly reflected by the surface of a cornea is converged. The miniature light source is positioned to have the converging point lie on the surface of an image of the fundus formed by the objective lens. Accordingly if the distance between the human eye and the instrument coincides with a preset distance, the image of the light source on the image surface of the objective lens becomes sharp. An operator looking into a view finder correctly adjusts the position of the instrument by moving the latter until the image of the light source becomes sharp.

22 Claims, 7 Drawing Figures

METHOD AND DEVICE FOR DETECTING DISTANCE BETWEEN EYE-EXAMINING INSTRUMENT AND EYE

BACKGROUND OF THE INVENTION

This invention relates to an eye testing and examining instrument such as an eye-fundus camera, an ophthalmoscope, etc. and more particularly to a method and a device for adjustment of a working distance between a human eye and an objective lens of such an instrument.

Spacing an eye examining instrument from the front of a human eye such as a cornea or an iris substantially affects the quality of the resulting image. Such spacing has heretofore been carried out by having the instrument moved by an operater who looks through a view finder in the optical axis direction of its objective lens until a flare or a ghost disappears from view.

However, when a flare is slight, the observer tends not to notice it and takes a photograph under incorrectly spaced conditions. Thus such flares often escape the observers' notice until after a photograph is finished. A photograph with such a flare is not usable for an accurate diagnosis.

Further, adjustment of such an instrument into a position in which there arises no flare or ghost arises not only takes time but also requires some skill and is not easy for observers.

On the other hand, there is known a device which illuminates an eye with an invisible light such as infrared rays or a very weak visible light; then detects a beam coming from the eye with a pick-up tube; and displays an electrical signal coming from the pick-up tube on a display surface of a cathode ray tube as an image of the eye. However, with such a device, a flare or ghost can be hardly detected, because a cathode-ray tube or an image intensifier used for such a purpose has a low resolving power and is inferior in sharpness or because the image is in a monochromatic light. Therefore, it has been often difficult to adjust a working distance with such a device.

SUMMARY OF THE INVENTION

It is an object of this invention to provide a method and a device for detecting whether a spacing distance between an eye-examining instrument and a human eye is meeting an optimum condition or deviating therefrom.

Another object of this invention is to provide a method and a device for permitting simultaneous observation of an image of a part of a human eye being examined and visible information on a working distance. This object is particularly important for an eye-fundus camera, because: focusing adjustment of a camera and adjustment of working distance must be carried out separately; however, the working distance tends to change while focusing adjustment is being made or defocusing tends to take place while the working distance is being adjusted. To avoid such, therefore, it is desirable to have information on the focus and information on the working distance simultaneously displayed on the same picture for confirmation of correct adjustment of the two.

A further object of this invention is to provide a method and a device for effecting alignment of a pupil center of a human eye with an optical axis subordinately to adjustment of the working distance.

The above and other related objects and features of this invention will be apparent from the following description of preferred embodiments taken in connection with the accompanying drawings.

DETAILED DESCRIPTION OF PREFERRED EMBODIMENTS

Figures 1, 2:
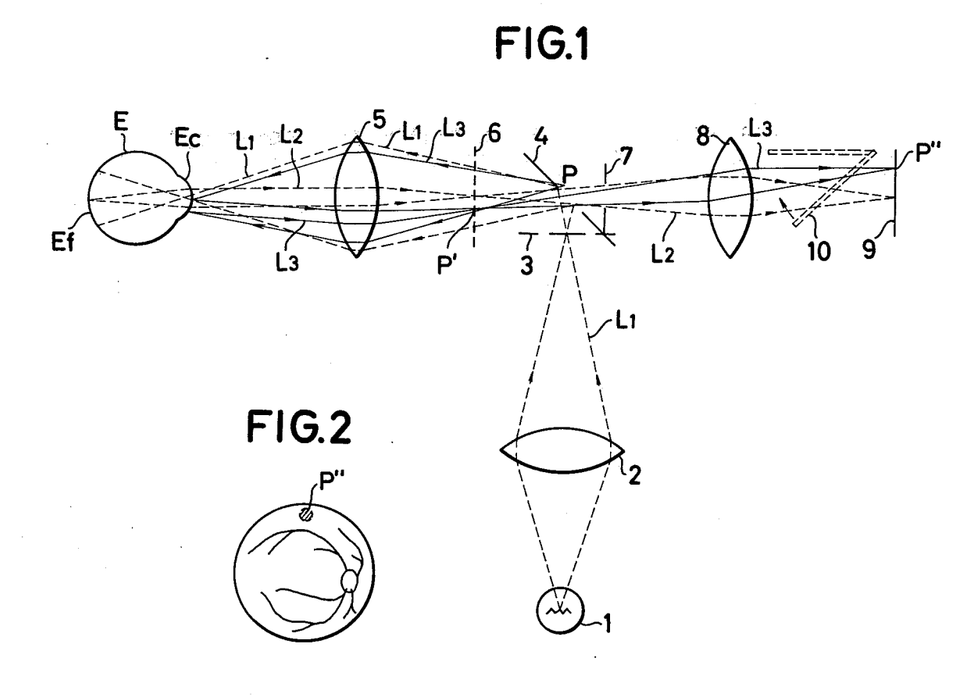
FIG. 1 is a sectional view illustrating an embodiment of this invention.
FIG. 2 is a plane view illustrating an image formed on a film.

FIG. 1 illustrates an essential part of an optical system for detecting a working distance as an embodiment of the invention. In FIG. 1, a reference symbol E indicates an eye to be examined; Ef indicates an eye-fundus or retina; and Ec indicates a cornea. In this particular embodiment, the fact that the surface of the cornea acts like a convex spherical mirror is utilized. Reference numeral 1 indicates a light source such as a lamp; 2 indicates a condenser lens; 3 indicates a slit plate provided with an annular opening, the light source 1 and the slit plate 3 being conjugate with each other in relation to the condenser lens 2; 4 indicates a perforated mirror which is provided with an aperture; and 5 indicates an objective lens. The perforated mirror 4 is obliquely arranged in relation to an optical axis of the objective lens and serves to direct the light of the light source 1 to the rear side of the objective lens 5. A reference numeral 6 indicates an image surface of the objective lens 5. An image of the eye fundus Ef of a normal eye is formed on the image surface of the objective lens 5. A reference numeral 7 indicates an aperture stop; 8 indicates an image forming lens; 9 indicates an image surface; and 10 indicates a quick return mirror. The image forming lens 8 serves to image the image of the image surface 6 on the image surface 9. The aperture stop 7 is conjugate with the slit plate 3 in relation to the perforated mirror 4. A view finder and an adjustment mechanism of the device are omitted from the illustration. A symbol P indicates an index of a given shape. The index P is either a miniature lamp or a projected image of a miniature lamp and is disposed at a position which is determined as follows: The rays L3 emitted from the index P is converged by the objective lens 5 and comes to be incident upon the cornea Ec. Regular (specular) reflection of these rays takes place at the cornea Ec and the reflected rays come to be incident upon the objective lens to be converged thereby. The position of the index P is set in such a manner that a converging point P' of these rays L3 comes to coincide with the image surface of the objective lens 5 when the distance between the objective lens 5 and a human eye E satisfies an optimum condition.

Referring to FIG. 1, the rays L1 from the light source 1 is converged on the annular slit of the slit plate 3 by the condenser lens 2. The converged rays L1 pass through the slit and then are reflected by at the perforated mirror 4 to diverge. Following this, the objective lens 5 causes the rays to converge on the cornea or in the vicinity of the iris of the human eye E to form an image of the annular slit there and the eye fundus Ef is illuminated thereby.

The eye fundus Ef then diffusedly reflects rays L2, which, after being emitted from the cornea Ec, are imaged by the objective lens 5 on the image surface 6 (a first conjugate face of the eye fundus). Then, the rays L2 pass through the aperture of the perforated mirror 4 and the aperture stop 7 one after another to be imaged on the image surface 9 by the image forming lens 8. The image surface is a second conjugate face of the eye fundus.

The mirror 10 which is obliquely arranged between the image forming lens 8 and the image surface 9 reflects the rays to guide the rays to an unillustrated view finder. This allows an observer looking into an eyepiece of the view finder to see an image of the eye fundus formed by the image forming lens 8.

In FIG. 1, the optical paths L1 and L2 indicated by broken lines respectively correspond to an illumination optical path and a photographing optical path of ordinary ophthalmoscopic optical system.

Then, the rays L3 emitted from the index P are converged by the objective lens 5 to be incident upon the cornea Ec; and are regularly reflected by the surface of the cornea into the reverse direction to be incident upon the objective lens 5. These rays form an image P' of the index P. If the distance between the eye E and the objective lens 5 is coinciding with a preset distance, the image P' then appears on the image surface 6 (or the first conjugate face of the eye fundus).

Further, the rays L3 pass through the aperture of the perforated mirror 4, the aperture stop 7 and the image forming lens 8 to form an image P" of the index P on the image surface 9 (or the second conjugate face of the eye fundus). Accordingly, there appear the image of the eye fundus and the image P" of the index on the second conjugate face as illustrated in FIG. 2.

When the images of the eye fundus and the index are observed by the observer looking into the view finder, if the distance between the eye E and the objective lens is equal to the preset distance, the image P" of the index appears sharp and crisp. If not, the image P" of the index appears blur and diffuse. If the observer finds the image P" blur and diffuse, he adjusts the position of the whole device by moving it in the direction of the optical axis until the image P" becomes sharp. The optimum distance is met when the image P" of the index P is made to be sharp through such adjustment. Further, the image P" of the index P is larger when it is blured than when it is sharp. On the other hand, the device also permits adjustment of alignment.

Figures 3, 4, 5:
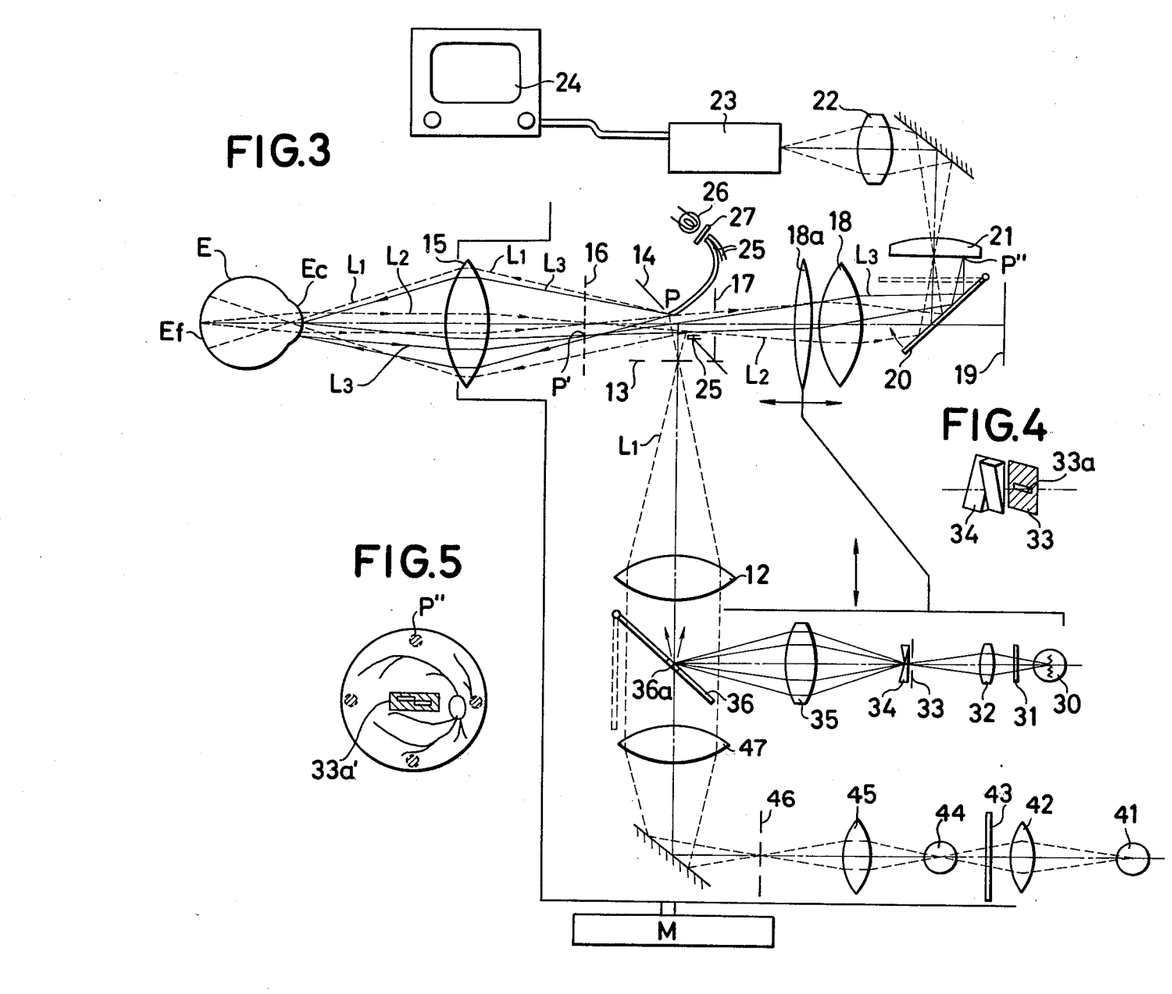
FIG. 3 is a sectional view illustrating an eye-fundus camera to which this invention is applied.
FIG. 4 is an oblique view illustrating a beam splitting means.
FIG. 5 is an illustration of an image displayed on a cathode ray tube.

Although there is indicated only one index, a plurality of such indexes may be symmetrically arranged around the optical axis in such a manner as to permit the use of it as auxiliary means for making the optical axis of the objective lens coincide with the optical axis of the eye being examined for a person whose cornea has a normal curvature. FIG. 5 illustrates an example wherein four indexes are employed and wherein the optical axis of the objective lens coincides with that of the eye being examined. With the optical axes of the objective lens and the eye coinciding with each other, the images P" of these indexes symmetrically appear having the middle part of the observation field at the center of their configuration. If these optical axes are not coinciding with each other, these images of indexes asymmetrically appear or some of them do not appear at all, so that the status of alignment between the eye being examined and the objective lens can be readily detected.

Normally, these indexes are arranged in positions slightly away from the optical axis so as not to hinder observation and photographing. However, in cases where the working distance and the alignment are to be adjusted through the use of only one index, the index may be arranged on the optical axis.

FIG. 3 is an illustration of an eye-fundus camera to which the present invention is applied. In this embodiment example, an invisible light such as infrared rays is used for focusing and a light which is emitted from an end face of each glass or plastic optical fiber is employed as an index. As for focusing means, the same means as disclosed in U.S. Pat. No. 3,925,793 may be employed.

In FIG. 3, a reference numeral 41 indicates a tungsten filament lamp; 42 indicates a condenser lens; 43 indicates a filter which transmits infrared or near infrared rays but shuts off visible light; 44 indicates a Strobo tube; 45 indicates a condenser lens; and 46 indicates a slit plate provided with an annular slit therein. The tungsten filament lamp 1 and the Strobo tube 4 are conjugate with each other in relation to the condenser lens 2 while an image of the tungsten filament lamp 1 and the Strobo tube 4 are conjugate with the slit plate 6 in relation to the condenser lens 5. A reference numerals 47 and 12 indicate relay lenses; and 13 indicates another slit plate provided with an annular slit. It is possible to use only one of the slit plates 6 and 13 while the other may be dispensed with. A reference numeral 14 indicates a perforated mirror provided with a circular aperture therein; 15 indicates an objective lens; 17 indicates an aperture stop which shuts off all light fluxes but a photographing light flux; and 18 and 18a indicate image forming lenses. The lens element 18a is movable in the optical axis direction for focusing. A reference numeral 19 indicates a film, 20 indicates a quick return mirror; 21 indicates a field lens the flat face of which is conjugate with the film 19 in relation to the quick return mirror 20; 22 indicates a photographing lens; 23 indicates a pick-up tube which is sensitive to infrared rays, the photo detecting surface of the pick-up tube 23 being conjugate with the bottom face of the field lens 21 in relation to the photographing lens 22; and 24 indicates a cathode ray tube such as a Braun tube. A reference symbol P indicates an index which is provided at the tip of an optical fiber. A reference numeral 25 indicates the optical fiber; 26 indicates a tungsten filament lamp; and 27 indicates a filter which allows infrared rays to pass through it but shuts off visible rays. The rays emitted from the lamp 26 pass through the filter 27 and come to be incident on one end face of each of the optical fibers 25 and passing through the fiber come out of the other end of the fiber. A reference numeral 30 indicates a tungsten filam nt lamp; 31 indicates another filter which transmits infrared rays but shuts off visible rays; 32 indicates a condenser lens; 33 indicates a slit plate having a rectangular slit provided therein, the slit plate 33 and the lamp 30 being conjugate with each other in relation to the condenser lens 32; and 34 indicates a bi-prism. FIG. 4 illustrates the bi-prism 34 and the slit plate 33 in a state of being separated. However, actually, they are closely adjacent to each other. A numeral 35 indicates a relay lens; 36 indicates a transparent flat plate and is provided with a partial mirror 36a; and the partial mirror 36a is conjugated with the slit plate 33 in relation to the relay lens 35. The above stated parts 30 through 36 are combined into one united body, which is movable in the optical axis direction of the relay lenses 47 and 12 in an interlocked relation with the element 18a. As a results of such arrangement, the film 19 and the slit plate 33 are maintained to be conjugate with each other in relation to the eye fundus Ef. A reference symbol M indicates a mechanism which carries a housing containing the optical system of the eye-fundus camera therein and which permits adjustment of the position of the camera by moving it left and right and back and forth.

With arrangement made as mentioned in the foregoing, when the lamp 26 is lighted, each of the four end faces of the optical fibers 25 emits infrared rays. The rays emitted from one end P of each of these optical fibers forms an image P' on the first conjugate face 16 of the eye fundus through the same process as described in the embodiment illustrated in FIG. 1. In this example, however, the infrared rays emitted through other fibers also form their point-like images on the first conjugate face.

When the element lens 18a is set in such a manner as to make the image surface 16 and the film surface 19 conjugate with each other in relation to the lenses 18 and 18a, a sharp image P" is formed, on the second conjugate face of the eye fundus, from each of the point images P'. In an eye-fundus camera, while distance to an object only slightly varies with the movement of the element lens 18a, the reflection image P' of each index shifts to a great extent in the optical axis direction as the working distance varies. Therefore, the element lens 18a does not have to be set into a preset position each time, because the error in the adjustment of the working distance arises only to a negligible degree.

Next, when the lamp 30 is lighted, only infrared rays among the rays emitted from the lamp 41 are allowed to pass through the filter 31. Then, the infrared rays which have passed through the filter 31 come to illuminate the eye fundus Ef through an illumination optical path L1. A flux or beam of light reflected at the eye fundus Ef comes through the photographing optical path L2 to form an image of the eye fundus on the second conjugate face of the eye fundus.

When the lamp 30 is lighted, the infrared rays which pass through the filter 31 are caused by the condenser lens 32 to converge on the slit plate 33. Then, the rays which have passed through the slit plate 33 are divided by the bi-prism 34 into two beams of light. Each of the divided light fluxes is caused by the relay lens 35 to converge on the partial mirror 36a, which reflects it toward the relay lens 12. The two light beams are converged by the relay lens 12 and are reflected by the perforated mirror 14 to converge on the image surface 16. Then, the lens 15 causes the two beams of light to converge on the eye fundus Ef. At this moment, if the eye fundus Ef is conjugate with the slit plate 33, an image of the slit 33a appears on the eye fundus Ef as it is. However, if not, the image of the slit 33a appears there being split into two from the middle part of the images. This is because: If they are not in a conjugate relation, the eye fundus Ef shuts off the light fluxes before these beams of light come to coincide with each other. In such a case, the position of the slit plate 33 is shifted to make the split half images into one image and thus to make the slit plate 33 conjugate with the eye fundus Ef.

Such shifting of the slit plate 33 is effected by moving it together with the other members of the system 30–36 including the slit plate 33. Since this system 30–36 is interlocked with the element 18a, conjugation or non-conjugation of the eye fundus is conjugate with the film 19 can be also found through the shape of the image of the slit 33a. Further, the beam of rays which has formed the image of the slit 33a is reflected by the eye fundus Ef and then passes through the optical path L1 to form another image on the second conjugate face of eye fundus (bottom face of field lens 21). Therefore, the images P" of the indexes P, the image of the eye fundus and the image of the slit 33a are formed on the light receiving face of the pick-up tube 23 through the lens 22 and then are displayed on the cathode ray tube 24. FIG. 5 illustrates a visible image displayed on the tube 24 showing the image of the eye fundus, the images P" of the indexes and the image 33a' of the slit 33a.

The observer who is watching the display surface of the tube 24 sees the images as shown in FIG. 5. He adjusts the mechanism M to make the images P" of the indexes sharp to effect adjustment of the distance between the eye E and the objective lens 15 to the optimum distance; and also, in the same manner, adjust the position of the element lens 18a until the split halves of each images 33a' are united into one image. When the images of the indexes are adjusted to their preset positions in the field and they are made to be sharp and when each of the split images are brought back into its original state, an unillustrated release button is operated to pull the transparent flat plate 36 and the quick return mirror 20 away from the optical path; and the Strobo tube 4 is caused to emit light to expose the film 19 to a reflected light coming from the eye fundus.

Figure 6:
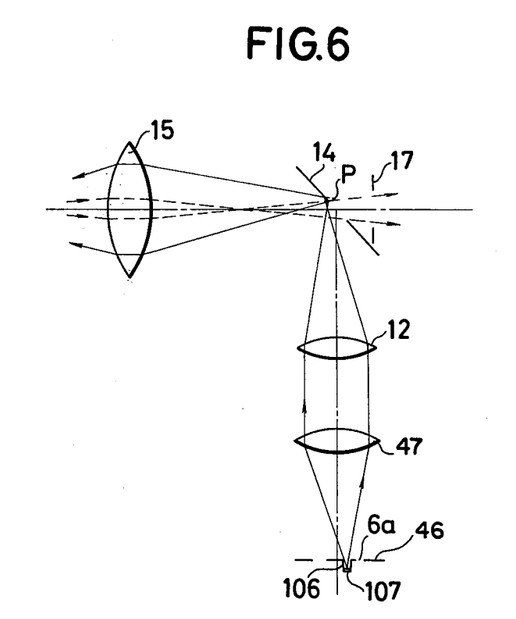
FIG. 6 is a partially sectional view illustrating another embodiment of the invention.
Figure 7:
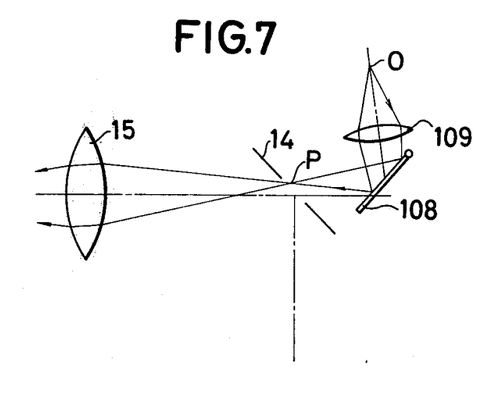
FIG. 7 is a partially sectional view illustrating a further embodiment of the invention.

In the foregoing embodiment example, the tip of each optical fiber arranged close to the perforated mirror 14 is used as an index. However, such arrangement may be replaced with provision of a miniature lamp or a light emitting diode, or an image of a light source may be projected onto the same position. FIG. 6 and FIG. 7 respectively illustrate examples wherein images of light sources are employed as indexes.

FIG. 6 illustrates a part of the illustration made in FIG. 3. In FIG. 6, a tube 106 is attached to a light shielding part provided in the middle of a slit plate 46 which is provided with an annular slit 6a. At the tip of the tube 106, there is provided an infrared filter 107 for the purpose of preventing visible rays from passing through there when light is emitted from the Strobo tube.

When the slit plate 46 is illuminated by an observation light beam or flux which is not illustrated, the beam of light which has passed through the filter 107 form an image P near to a perforated mirror 14. This image P corresponds to the index P shown in FIG. 1. The filter 107 may be replaced with a lamp.

In FIG. 7 which illustrates another projection system arrangement, a reference numeral 108 indicates a half-transparency mirror; 109 indicates a relay lens; and 0 indicates either a miniature lamp or an aperture of a preset shape, the aperture 0 being illuminated. A beam of light coming from the light source or the secondary light source 0 is converged by a lens 109 and is reflected to form an image P, which is used as an index. At the position of 0, if there is provided an annular aperture to form an image of the aperture on a plane on the extension of the optical axis of an objective lens 15, an annular index appears in the field of view. In other words, with such arrangement, a bright ring appears encircling the split image 33a' shown in FIG. 5. The image of the index is arranged close to the image 33a' of the slit for the purpose of permitting simultaneous observation of the two.

What is claimed is:

1. A device for detecting the distance between an eye-examining instrument and an eye comprising:
   an inspecting system for inspection of a human eye, said system having a front optical means confronting the human eye;
   means for forming at least one index; and
   said front optical means being arranged for converging a beam of light emitted from said index to a degree required for illumination of the front part of the human eye with the beam of light and also for allowing said front optical means to converge, substantially on an image surface of said front optical means, a beam of light reflected by the front of the human eye arranged at a predetermined position.

2. A device according to claim 1, wherein said index emits a beam of light through said front optical means for specular reflection thereof by the human eye.

3. A device according to claim 1 wherein said means for forming the index is provided with at least one optical fiber and a light source for illuminating one end of the optical fiber.

4. A device according to claim 1 wherein said means for forming the index is provided with at least one light source and a projection lens means.

5. A device according to claim 1 wherein said inspecting system is provided with a viewer.

6. A device according to claim 5 wherein said viewer is provided with image display means.

7. A device according to claim 1, in which said means for forming the index forms a plurality of indices symetrical to the optical axis of said inspecting system.

8. A device according to claim 1, in which said inspecting system has a photographic apparatus and an illuminating apparatus and a viewer for viewing the eye fundus, first beam selecting means for optically coupling said photographic apparatus and said illuminating apparatus and second beam selecting means for optically coupling said viewer to said photographic apparatus, and wherein said means for forming the index forms a plurality of indices adjacent said first beam selecting means.

9. A device according to claim 8, said means for forming the index is provided with optical fibers having ends and illuminating means for illuminating the ends of said optical fibers.

10. A device according to claim 8, wherein said means for forming the index is provided with at least one miniature lamp.

11. A method for detecting a proper distance between an eye-examining instrument and an eye, which method comprises:
   forming an index at a preset position;
   illuminating the cornea of the human eye with a beam of light emitted by said index through objective optical means of said instrument;
   converging the beam of light which is reflected by the cornea with said objective optical means; and
   adjusting the position of said instrument along the optical axis of said objective optical means to bring a converging point of the beam of light to an image surface of said objective optical means.

12. A method according to claim 11 wherein a plurality of indexes are formed and symmetrically arranged around the optical axis of the objective optical means with the optical axis in the center of the arrangement.

13. A device for arranging an opthalmic instrument relative to the eye comprising:
   an inspecting system for inspection of the human eye and for focusing on the eye fundus, said system including a front optical means facing the human eye; a mark projection means for projecting a marking beam to the cornea of the human eye; and an observing apparatus optically coupled with said inspecting system for observing the image of the mark; the marking beam being specularly reflected by the cornea and forms an image on a plane substantially conjugate to the eye fundus in respect of said front optical means when the cornea is a predetermined distance from the front optical means.

14. A device according to claim 13, in which said inspecting system comprises a photographic apparatus and an illuminating apparatus for illuminating the eye fundus.

15. A device for arranging an opthalmic instrument relative to the eye comprising:
   a photographic system able to focus on the eye fundus, comprising an objective, an image forming lens and an image recording means;
   a viewer for viewing an image plane formed by said photographic system;
   beam selecting means arranged between said image forming lens and said image recording means and being arranged to couple to said photographic system and said viewer;
   an illuminating system optically coupled to said photographic system to illuminate the eye fundus;
   index forming means for forming at least one index and arranged so that a beam from the index is reflected on the cornea of the eye to form an image on said image plane when the cornea of the eye is a predetermined distance from the objective.

16. A device according to claim 15, wherein said index forming means comprises at least one optical fiber and a light source.

17. A device according to claim 15, wherein said index forming means comprises at least one light source and a projection lens.

18. A device according to claim 15, wherein said index forming means includes a light source.

19. A device according to claim 15, wherein said index emits an infra red light beam.

20. A device according to claim 15, wherein said index forming means includes a plurality of indices symetrical to the optical axis of said photographic system.

21. A device according to claim 15, wherein said viewer includes a relay lens, a television-camera and television-display apparatus.

22. An opthalmic instrument comprising:
   an eye inspecting apparatus capable of focusing on an eye fundus, including objective and imaging optics;
   an observing apparatus coupled to said eye inspecting apparatus for observing an image surface of said imaging optics;
   mark projection means coupled to the eye inspecting apparatus for projecting a marking beam so that the marking beam is specularly reflected by the cornea of the eye and falls on the image surface; and
   adjusting means for adjusting the distance between the eye and said eye inspecting apparatus so as to make the image of the mark in the view field of said observing apparatus clear.

* * * * *

REEXAMINATION CERTIFICATE (94th)

United States Patent [19]
Kohayakawa et al.

[11] B1 4,196,979
[45] Certificate Issued Jun. 14, 1983

[54] METHOD AND DEVICE FOR DETECTING DISTANCE BETWEEN EYE-EXAMINING INSTRUMENT AND EYE

[75] Inventors: Yoshimi Kohayakawa; Isao Matsumura, both of Yokohama, Japan

[73] Assignee: Canon Kabushiki Kaisha, Tokyo, Japan

Reexamination Request
No. 90/000,117, Nov. 30, 1981

Reexamination Certificate for:
Patent No.: 4,196,979
Issued: Apr. 8, 1980
Appl. No.: 832,827
Filed: Sep. 13, 1977

[30] Foreign Application Priority Data

Oct. 16, 1976 [JP] Japan .................... 51-124289
May 30, 1977 [JP] Japan .................... 52-63065

[51] Int. Cl.$^3$ ............................. A61B 3/14
[52] U.S. Cl. .......... 351/208; 351/211; 354/62; 356/3
[58] Field of Search ... 351/1, 7, 6, 13, 14, 16, 208; 356/3, 8, 20; 354/62

[56] References Cited

U.S PATENT DOCUMENTS

| | | | |
|---|---|---|---|
| 3,538,754 | 11/1970 | Grolman et al. | 73/80 |
| 3,796,220 | 3/1974 | Bredemeier | 128/303.1 |
| 3,880,501 | 4/1975 | Munnerlyn | 351/8 |
| 4,068,932 | 1/1978 | Ohta et al. | 351/7 |

FOREIGN PATENT DOCUMENTS

| | | |
|---|---|---|
| 2415319 | 9/1976 | Fed. Rep. of Germany. |
| 39-24147 | 10/1964 | Japan. |
| 40-17707 | 8/1965 | Japan. |
| 49-17294 | 4/1974 | Japan. |

*Primary Examiner*—F. L. Evans

[57] ABSTRACT

A method and a device for making the distance between a human eye and an eye-examining instrument coincide with a preset distance. A miniature light source disposed on the image end of an objective lens of the instrument illuminates the eye. The light specularly reflected by the surface of a cornea is converged. The miniature light source is positioned to have the converging point lie on the surface of an image of the fundus formed by the objective lens. Accordingly if the distance between the human eye and the instrument coincides with a preset distance, the image of the light source on the image surface of the objective lens becomes sharp. An operator looking into a view finder correctly adjusts the position of the instrument by moving the latter until the image of the light source becomes sharp.

REEXAMINATION CERTIFICATE ISSUED UNDER 35 U.S.C. 307.

THE PATENT IS HEREBY AMENDED AS INDICATED BELOW.

Matter enclosed in heavy brackets appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 13, 14, and 22 is confirmed.

Claims 1, 11, and 15 are determined to be patentable as amended:

1. A device for detecting the distance between an eye-examining instrument and an eye comprising:
   an inspecting system for inspection of a human eye, said system having a front optical means confronting the human eye;
   means for forming at least one index;
   said front optical means being arranged for converging a beam of light emitted from said index to a degree required for illumination of the front part of the human eye with the beam of light and also for allowing said front optical means to converge, substantially on an image surface of said front optical means, a beam of light reflected by the front of the human eye arranged at a predetermined postition [.] *and the image surface of the front optical means being out of the condition of being conjugate to the front of the human eye with respect to the front optical means.*

11. A method for detecting a proper distance between an eye-examining instrument and an eye, which method comprises:
   forming an index at a preset position;
   illuminating the cornea of the human eye with a beam of light emitted by said index through objective optical means of said instrument;
   converging the beam of light which is reflected by the cornea with said objective optical means; and
   adjusting the position of said instrument along the optical axis of said objective optical means to bring a converging point of the beam of light to an image surface of said objective optical means [.] *and the image surface of the objective optical means being out of conjugacy to the cornea with respect to the objective optical means.*

15. A device for arranging an opthalmic instrument relative to the eye comprising:
   a photographic system able to focus on the eye fundus, comprising an objective, an image forming lens and an image recording means;
   a viewer for viewing an image plane formed by said photographic system;
   beam selecting means arranged between said image forming lens and said image recording means and being arranged to couple to said photographic system and said viewer;
   an illuminating system optically coupled to said photographic system to illuminate the eye fundus;
   index forming means for forming at least one index and arranged so that a beam from the index is *specularly* reflected on the cornea of the eye to form an image on said image plane when the cornea of the eye is a predetermined distance from the objective.

Claims 2–10, 12, and 16–21 dependent on amended claims, are determined to be patentable.

New claims 23–35 are added and determined to be patentable.

*23. A device as in claim 1, wherein said front optical means has a defined structure along an optical axis and said index is located so that light from said index travels from behind said front optical means through the front optical means to the front of the eye.*

*24. A device as in claim 1, wherein said front optical means includes a lens having an optical axis to be aligned with the eye and for converging the beam of light from the index and simultaneously defining the image surface along the optical axis, said lens being located between the index and a location for the eye to be examined.*

*25. A device as in claim 24, wherein the image surface occurs in front of the index relative to the front optical means.*

*26. A device as in claim 24, further comprising second optical means having a second lens behind the front optical means and having an optical axis coaxial with the optical axis of said front optical means for focusing images on the image surface onto a second image surface behind said second optical means.*

*27. The method as in claim 11, wherein a lens in said objective optical means converges the beam of light reflected by the cornea and passes the beam of light emitted by the index.*

*28. The method as in claim 27, wherein second optical means focus the image surface of said objective optical means on a second image surface.*

*29. A device as in claim 13, wherein said front optical means have a defined optical axis, and wherein said mark projection means is located so that light from said mark projection means travels from behind said front optical means through the front optical means to the cornea of the eye.*

*30. A device as in claim 13, wherein said front optical means includes a lens having an optical axis to be aligned with the eye and for converging light from the projection means and simultaneously defining the image surface along the optical axis, said lens being located between the mark projection means and a location for the eye to be examined.*

*31. A device as in claim 13, wherein the image surface occurs in front of the projection means relative to the front optical means.*

*32. A device as in claim 31, further comprising second optical means having a lens behind the front optical means and having an optical axis coaxial with the optical axis of said front optical means for focusing images on the image surface onto a second image surface behind said second optical means.*

*33. A device as in any one of claims 1, 23, 24, 25, or 26, wherein said front optical means is arranged simultaneously to form an image of the fundus of the eye on the image surface.*

34. The method as in claim 11, 27, or 28, further comprising the step of simultaneously forming an image of the fundus of the eye on the image surface.

35. A device as in any one of claims 13, 29, 30, 31, or 32, wherein said front optical means are arranged simultaneously to form an image of the fundus of the eye on the image surface.

* * * * *